United States Patent
Fatiny

(10) Patent No.: US 10,321,973 B1
(45) Date of Patent: Jun. 18, 2019

(54) COMPOSITE RESTORATION CONDENSER WITH ROLLING BALL TIP

(71) Applicant: King Abdulaziz University, Jeddah (SA)

(72) Inventor: Fahad Ibrahim Fatiny, Jeddah (SA)

(73) Assignee: King Abdulaziz University, Jeddah (SA)

( * ) Notice: Subject to any disclaimer, the term of this patent is extended or adjusted under 35 U.S.C. 154(b) by 12 days.

(21) Appl. No.: 15/822,708

(22) Filed: Nov. 27, 2017

(51) Int. Cl.
*A61C 1/12* (2006.01)
*A61C 3/08* (2006.01)

(52) U.S. Cl.
CPC . *A61C 1/12* (2013.01); *A61C 3/08* (2013.01)

(58) Field of Classification Search
CPC .... A61C 3/00; A61C 3/08; A61C 5/04; A61C 5/045; A61C 19/004; A61H 13/00
USPC ................................. 433/141, 156, 164, 163
See application file for complete search history.

(56) References Cited

U.S. PATENT DOCUMENTS

| | | | | |
|---|---|---|---|---|
| 1,252,179 A | * | 1/1918 | Risley | A61C 3/08 433/164 |
| 1,615,910 A | * | 2/1927 | Nuyts | A61H 13/00 601/129 |
| 2,263,802 A | * | 11/1941 | Grusin | A46B 3/00 15/110 |
| 4,586,901 A | | 5/1986 | Tanaka et al. | |
| 4,683,875 A | * | 8/1987 | Rabinowitz | A61H 13/00 601/141 |
| 6,931,688 B2 | * | 8/2005 | Moskovich | A46B 7/06 15/167.1 |
| 9,532,643 B2 | * | 1/2017 | Moskovich | A46B 9/04 |
| 2001/0016697 A1 | * | 8/2001 | Gorsen | A61H 13/00 601/80 |
| 2005/0196722 A1 | * | 9/2005 | Jessop | A61C 7/14 433/141 |
| 2008/0003052 A1 | * | 1/2008 | Lee | A45D 34/041 401/209 |
| 2011/0223559 A1 | | 9/2011 | Jamnia et al. | |
| 2014/0010583 A1 | * | 1/2014 | Boyd | A46B 11/002 401/220 |
| 2014/0228723 A1 | * | 8/2014 | Cockerill | A61H 15/0092 601/128 |
| 2014/0357982 A1 | | 12/2014 | Malul | |

(Continued)

FOREIGN PATENT DOCUMENTS

| | | |
|---|---|---|
| DE | 102 08 957 A1 | 9/2003 |
| DE | 10 2004 027 300 B4 | 1/2007 |
| GB | 169217 A * 9/1921 | ............. A61H 13/00 |

(Continued)

OTHER PUBLICATIONS

Translation of JP 1-291865.*

*Primary Examiner* — Wade Miles
*Assistant Examiner* — Matthew P Saunders
(74) *Attorney, Agent, or Firm* — Oblon, McClelland, Maier & Neustadt, L.L.P.

(57) ABSTRACT

A dental instrument with an elongated tip housing a ball within a socket. The exposed surface of the ball may be pressed against a restorative material on a tooth surface in order to evenly distribute the restorative material without incorporating air bubbles. A dental instrument may have a second elongated tip housing a ball on an opposing end. The elongated tip housing the ball may be removably attached or may be rotatable.

16 Claims, 8 Drawing Sheets

(56) References Cited

U.S. PATENT DOCUMENTS

2017/0128157 A1  5/2017  Muller et al.

FOREIGN PATENT DOCUMENTS

| GB | 218345 A | * | 7/1924 | ............ A61H 13/00 |
| JP | 1-291865 | * | 11/1989 | |

* cited by examiner

COMPOSITE RESTORATION CONDENSER WITH ROLLING BALL TIP

BACKGROUND OF THE INVENTION

Technical Field

The present invention relates to a dental instrument having a tip with a rolling ball for even distribution of a restorative material.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Standard filling and restoration materials in dentistry include composite materials that often contain binders in the form of hardened organic substances and fillers. Generally, dental restorative materials that are polymerizable with light must be applied within a short time frame because during their careful application and subsequent contouring, they can start to polymerize due to ambient light. Similarly, the application and contouring of dental restoratives that incorporate a chemical catalyst must also be completed before substantial polymerization of the restorative.

A disadvantage of these composite materials is their tendency to adhere to the instrument that is used to apply or shape them. As a result, the composite material has a tendency to be drawn off from the edges of the cavity, to be inhomogeneously distributed on the tooth surface, or to form air bubbles during the distribution.

While the clinical performance of dental composites has been significantly improved over the past decade through modifications in formulation that include using more stable polymerization promoters for greater color stability; incorporating high concentrations of finely ground fillers to produce adequate strength and excellent wear resistance while retaining translucency; adding radio pacifying agents for improved diagnostics; and utilizing dentin adhesives, there are still significant problems which limit the use of composites, especially in posterior teeth.

Many composite materials remain very technique-sensitive, due to the extensive contraction which accompanies polymerization and which negatively influences marginal sealing. In addition, composite materials are generally considered to have inadequate mechanical properties and wear resistance in contact areas to serve as total replacements for amalgams.

Current efforts have focused on development of non- or minimally-shrinking dental composites containing spiro-orthocarbonates as additives to dimethacrylates or epoxy-base resins, and the production of alternative filler materials for ideal wear resistance and aesthetics.

The instruments for distributing a restorative dental material typically comprise a steel instrument with an uncoated working tip portion or a tip portion coated with a metal alloy such as nickel-titanium. They may also be composed of a plastic material with or without working tip that is treated or coated with a non-stick material. For example, a dental instrument may be coated with TEFLON (polytetrafluoroethylene, or PTFE) to reduce adhesion of a restorative composite. However, even with such coatings, a restorative material may adhere or otherwise be difficult to apply.

Alternatively, it has been proposed to reduce composite adherence to a dental instrument by providing a discontinuous surface that includes an array of micro-pits, see U.S. Pat. No. 6,071,122. While that instrument achieves reduced adhesion of the composite material, distribution of composite that is both homogeneous and free of air bubbles has not been fully achieved and thus strength, durability, and aesthetic properties of a restoration are detrimentally affected.

Other potential approaches include the use of dental instruments with roller tips. For example, Besek, et al., U.S. 20050130099, describe a dental instrument with a monolithic roller tip which is mounted on an internal axial rotating member so that the monolithic tip can rotate around a longitudinal axis. However, this configuration can make the uniform application of a material difficult and may introduce air bubbles into the applied restorative material. These problems may be caused by rotation of the apex of the rotating tip which can produce sheer forces that result in mixing of a composite material and air or saliva, especially in or around narrow or confined dental surfaces.

Consequently, there is a need for a dental instrument that is effective for homogeneously distributing a composite restorative material to a tooth surface, which avoids the integration of air bubbles into a restoration, and thus provides superior strength, durability, color, and aesthetics to a completed restoration site.

In view of the foregoing, one objective of the present invention is to provide a dental instrument having a handle with a working end from which a curved and/or angled shank extends, supporting a socket housing a rotatable ball. The dental instrument may be manipulated to press and roll the exposed surface of the ball against a composite material, in order to evenly distribute the composite material without introducing air bubbles. The ball may be coated by or made with a non-stick material.

BRIEF SUMMARY OF THE INVENTION

According to a first aspect, the present disclosure relates to a dental instrument that has a handle with a working end, a curved and/or angled shank extending from the working end, an elongated tip with a socket, wherein the elongated tip is mounted on the curved and/or angled shank; and a ball rotatably housed within the socket, having an exposed surface configured to contact a dental composite.

In one embodiment, the elongated tip is cylindrical.

In one embodiment, the elongated tip is frustoconical with a larger diameter oriented towards the ball.

In one embodiment, the ball has an exposed surface area fraction of 0.25 to 0.42 relative to a total surface area of the ball.

In one embodiment, a ratio of a diameter of the ball to a largest outer diameter of the elongated tip is 7:10-19:20.

In one embodiment, a ratio of the smallest diameter of the shank to the largest outer diameter of the elongated tip is 3:10-4:10.

In one embodiment, the elongated tip is rotatably attached to the curved and/or angled shank.

In one embodiment, the elongated tip is removably attached to the curved and/or angled shank.

In one embodiment, an end of the elongated tip connected to the curved and/or angled shank has a beveled edge.

In one embodiment, a central axis of the elongated tip forms an angle of 0°-90° with a central axis of the handle.

In one embodiment, a central axis of the elongated tip forms an angle of 50°-75° with a central axis of the handle.

In one embodiment, the dental instrument also has a fluid line traversing from the socket to the handle.

In one embodiment, the socket has no more than one opening.

In one embodiment, the dental instrument also has a second angled shank extending from an end of the handle distal to the working end, having a second elongated tip with a second socket and a second ball rotatably housed within the second socket, having a second exposed surface. The ball and the second ball have unequal diameters.

In one embodiment, the handle, the curved and/or angled shank, the elongated tip, and/or the ball comprises metal.

In one embodiment, the handle, the curved and/or angled shank, the elongated tip, and/or the ball comprises a plastic which contains metal, glass, ceramic, carbon, or polymer fibers.

In one embodiment, the handle, the curved and/or angled shank, the elongated tip, and/or the ball is made of, contains, or is coated with a non-stick material.

In one embodiment, the handle, the curved and/or angled shank, the elongated tip, and/or the ball is made of, contains, or is coated with at least one of a silicone, a thermoplastic elastomer, or a polyurethane.

In one embodiment, the handle, the curved and/or angled shank, the elongated tip, and/or the ball is made of, contains, or is coated with at least one material having a Shore A hardness (ASTM D2240 00) ranging from 20-80.

According to a second aspect, the present disclosure relates to a method for distributing a restorative material on a surface of a tooth. This method involves the steps of applying the restorative material to the surface of the tooth to produce an applied restorative material and distributing the applied restorative material with the dental instrument of the first aspect.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF TIE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
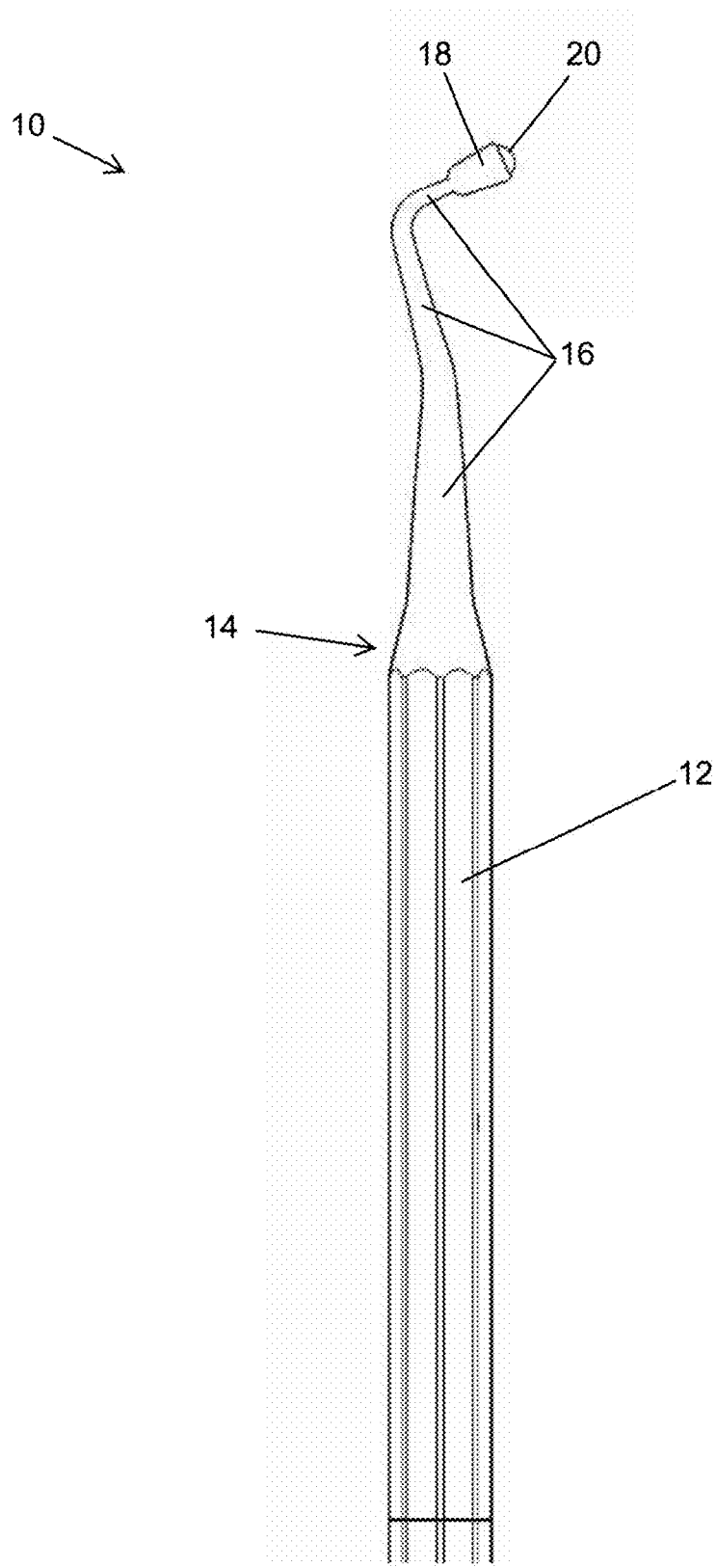
FIG. 1 is an embodiment of the dental instrument of the present disclosure.

Embodiments of the present disclosure will now be described more fully hereinafter with reference to the accompanying drawings, in which some, but not all embodiments of the disclosure are shown.

As used herein, the words "a" and "an" and the like carry the meaning of "one or more." Within the description of this disclosure, where a numerical limit or range is stated, the endpoints are included unless stated otherwise. Also, all values and subranges within a numerical limit or range are specifically included as if explicitly written out.

According to a first aspect, the present disclosure relates to a dental instrument 10 that has a handle 12 with a working end 14, a curved and/or angled shank 16 extending from the working end, an elongated tip 18 with a socket 24, the elongated tip mounted on the curved and/or angled shank; and a ball 20 rotatably housed within the socket, having an exposed surface configured to contact a dental composite.

As used herein, the handle 12 refers to an elongated portion of the dental instrument 10 which is configured so that it may be held in a hand. The more distal parts of the handle from its center point may comprise a tapering waist and a shoulder portion which form portions of, and help position, the curved and/or angled shank 16. The dental instrument handle 12 may have a length of 40-200 mm, preferably 70-180 mm, more preferably 80-150 mm, and a width or diameter of 4-30 mm, preferably 7-20 mm, more preferably 7-15 mm. Preferably the handle 12 is straight, but in an alternative embodiment the handle 12 may be curved and/or angled. Preferably the handle 12 is sterilizable by autoclave or other means. In one embodiment, the exterior surface of the handle may comprise a different material than its core or interior. The exterior surface of the handle may be polished or treated in a way to reduce glare or reflection. The handle may have a cylindrical shape or may have a prismatic shape, such as a hexagonal or triangular prism, to improve finger grip. In another embodiment, a portion of the handle may taper to a larger or smaller diameter, for example, the diameter of the handle may decrease away from the shank. To further improve finger grip, a portion or segments of the exterior surface of the handle may comprise ribs, ridges, grooves, knurls, bumps, or some other texture. The handle may have a cushion on the exterior surface for the same purpose. This cushion may comprise an elastomeric compound such as silicone rubber, latex, butyl rubber, neoprene, and/or nitrile, and may be solid or comprise air pockets. The cushion may have a height or thickness of 1 mm-4 mm, preferably 1.5-3 mm, more preferably 1.6-2 mm. The handle may also comprise a ruler, for example, markings on the exterior surface to show a scale of centimeters and/or millimeters. In an alternative embodiment, the handle may have a light source attached, such as an LED, for illumination within a patient's mouth.

Figure 3A:
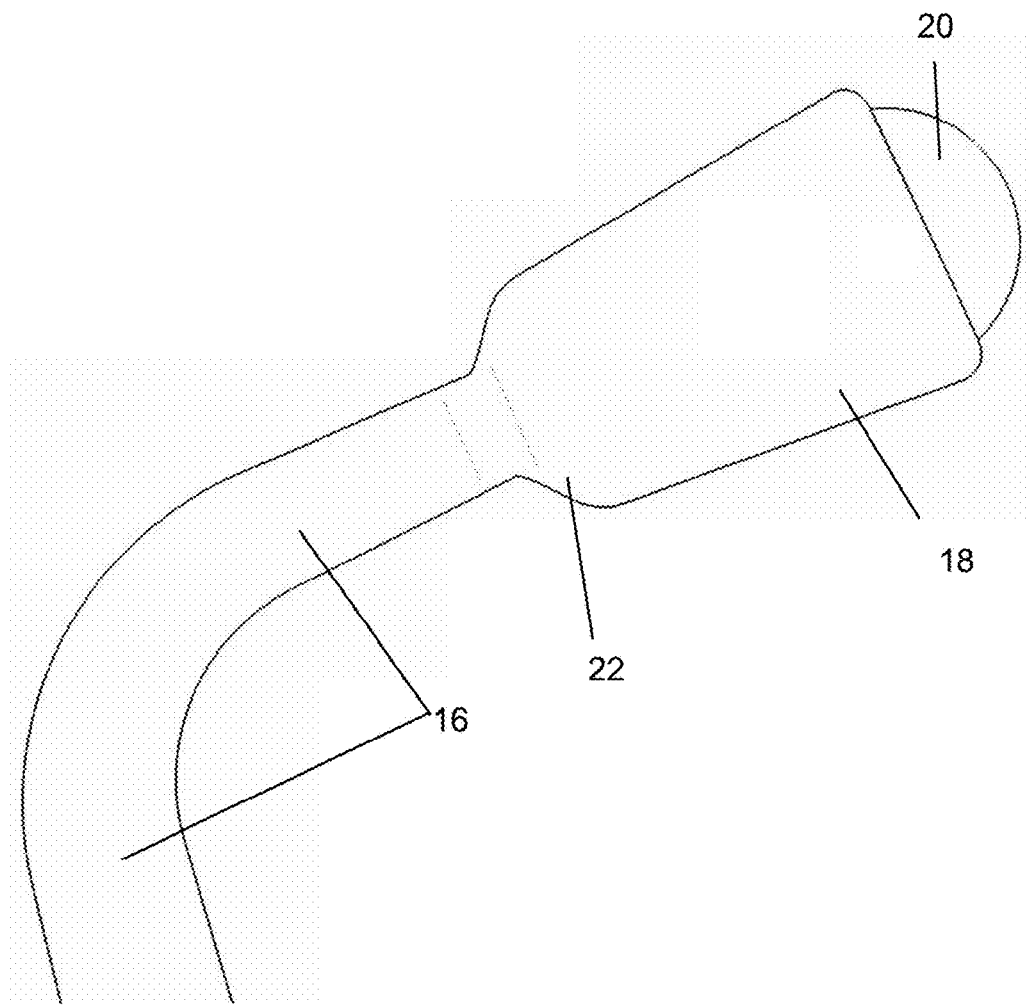
FIG. 3A is a side view of a dental instrument's working end.
Figure 3B:
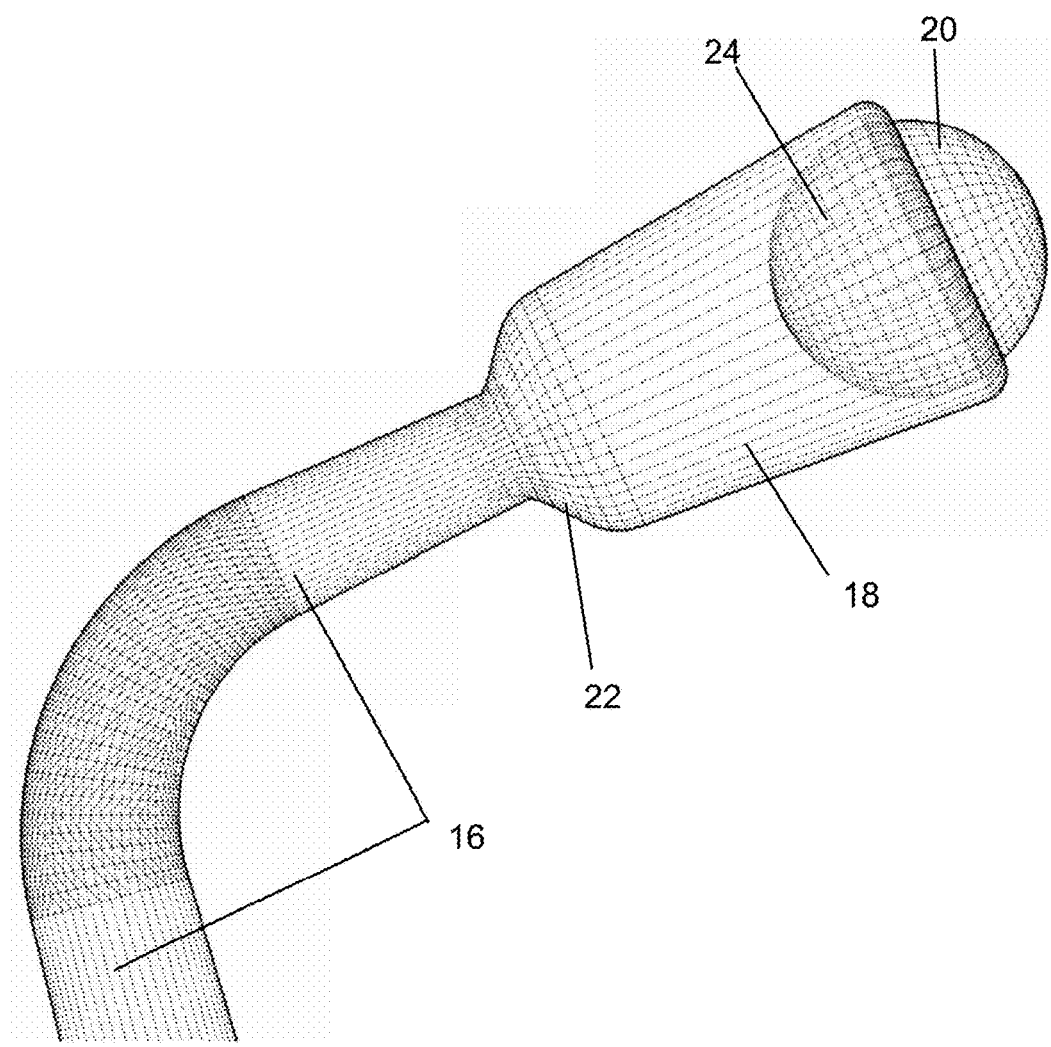
FIG. 3B is a wire-frame version of FIG. 3A, showing the socket and the entire ball.
Figure 6:
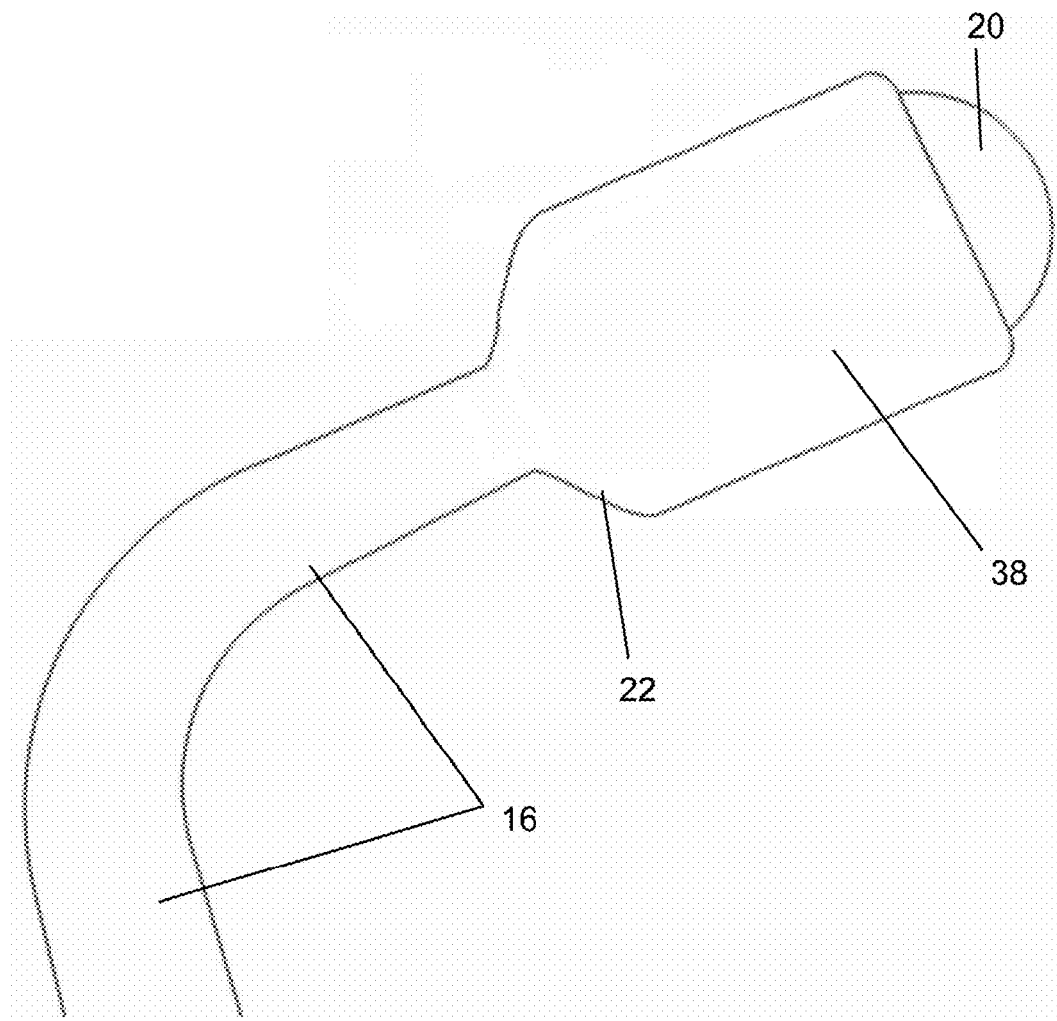
FIG. 6 is a dental instrument with a cylindrically shaped elongated tip.

In one embodiment, the elongated tip 18 is frustoconical with a larger diameter oriented towards the ball 20. A frustoconical solid describes a cone that has its top sliced off with a plane parallel to the plane of the base. In other words, a frustoconical solid is a frustum of a cone. In some embodiments, the ratio between the smallest diameter to the largest diameter of the frustoconical elongated tip 18 ranges from 1:1.05, 1:1.1, 1:1.3, 1:1.5, 1:2, 1:2.5, 1:3, 1:3.5, 1:4, 1:4.5, to 1:5, or any intermediate ratio. An exemplary ratio between the largest diameter and the smallest diameter is shown in FIGS. 3A and 3B. However, in some embodiments, the elongated tip is cylindrical 38, as shown in FIG. 6. A cylindrical elongated tip 38, or a frustoconical elongated tip 18, may or may not have a beveled edge 22.

In an alternative embodiment, the elongated tip may not be cylindrical or frustoconical. For instance, the elongated tip may be some other elongated shape such as a prism having a triangular base, a rectangular base, a hexagonal base, or some other base. The elongated shape may also be a truncated pyramid or some other shape with changing cross-section areas through its length. In other embodiments, the tip may not necessarily be elongated, and may be any structure or shape that is able to secure the ball 20 while allowing an exposed surface area where the ball 20 may contact and roll against a restorative material 42. For instance, the ball may be housed within a substantially spherical shape that has a single opening. Alternatively, the ball may be held in place by prongs, similar to a jewelry setting with the exception that the ball is freely rotatable.

Figure 2:
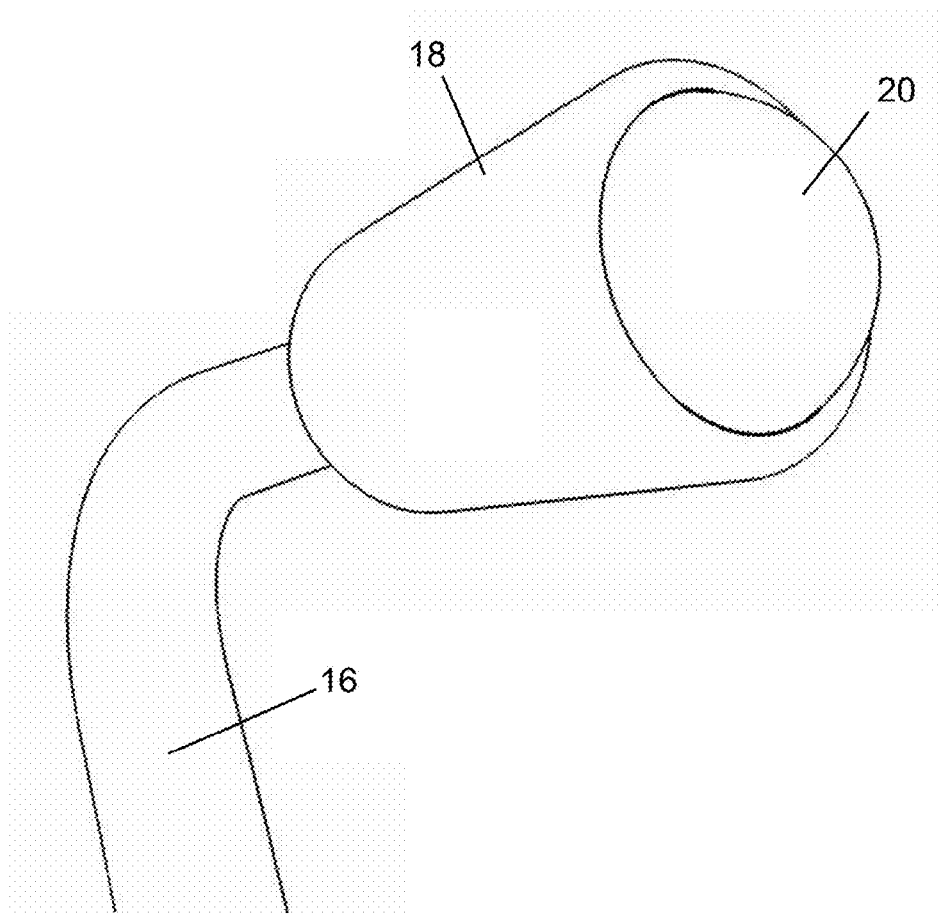
FIG. 2 is a perspective view of a dental instrument's working end.

In one embodiment, the ball 20 has an exposed surface area fraction of 0.25 to 0.42, preferably 0.30 to 0.40, more preferably 0.31-0.35 relative to a total surface area of the ball. This embodiment is shown in FIG. 3B, which shows the portion of the ball in the socket 24, and the portion of the ball exposed. FIG. 2 shows a perspective view of the elongated tip 18 and exposed surface area of the ball 20. Preferably, the ball 20 is smooth and substantially spherical, having an RMS surface roughness less than 10 µm, preferably less than 5 µm, more preferably less than 1 µm. However, in some embodiments the ball 20 may have micro- or nano-texturing to reduce adherence of materials or to otherwise facilitate homogenous application of a dental restorative material. In some embodiments, the smoothness or texturing of the ball is dependent on the material of the ball and the type of dental composite used. Additionally, in some embodiments, the ball 20 may have an exposed surface area fraction of less than 0.25 or greater than 0.42.

Preferably the ball 20 is freely rotatable in any direction, however, in one embodiment, the ball may be fixed to an axel inside the socket 24 in order to restrict its movement to rotation around a single axis. In a similar embodiment, a cylindrical roller having a height and/or diameter similar to the diameter of the ball may instead be fixed inside the socket 24, and may be fixed to rotate on its central axis.

In one embodiment, a ratio of a diameter of the ball 20 to a largest outer diameter of the elongated tip 18 is 7:10-19:20, preferably 15:20-18:20, more preferably 16:20-17.2:20, as shown in FIG. 3B. However, in some embodiments, the ratio may be smaller than 14:20 or larger than 19:20. Despite these ratios, it is preferable that the diameter of the socket opening is smaller than the diameter of the ball, in order to keep the ball 20 from falling out of the socket 24. The socket opening may have a flange or an inwardly curved lip that provides this smaller diameter and holds the ball in the socket. The ratio of the diameter of the socket opening to the diameter of the ball may be 70:100-98:100, preferably 80:100-96:100, more preferably 85:100-95:100, even more preferably 92:100-94:100, as is evident in FIG. 3B. Preferably the socket opening is circular; however, in alternative embodiments the socket opening may be different shapes that hold the ball inside the socket while providing an exposed, rotatable surface area. In one embodiment, the socket opening comprises an elastomeric material so that the ball can be pushed out from inside the socket, and then be reinserted or exchanged.

In one embodiment, a ratio of the smallest diameter of the shank 16 to the largest outer diameter of the elongated tip 18 is 3:10-4:10, preferably 3.2:10-3.8:10, more preferably 3.3:10-3.7:10, as shown in FIG. 3A. However, in some embodiments, the ratio may be smaller than 3:10 or larger than 4:10.

In one embodiment, the ratio of the largest outer diameter of the elongated tip 18 to the longitudinal length of the elongated tip is 1:10-5:10, preferably 2:10-4.5:10, more preferably 3:10-4:10, or about 2:3, as shown in FIG. 3A. Here, the longitudinal length includes the beveled portion or beveled edge 22, if such structure is present. In other embodiments, the ratio of the largest outer diameter of the elongated tip to the longitudinal length of the elongated tip may be smaller than 1:10 or greater than 5:10.

In one embodiment, the elongated tip 18 is rotatably attached to the curved and/or angled shank 16. Here, the elongated tip may be circumferentially rotatable around the central axis of the elongated tip, in relation to the shank. Preferably, the central axis of the shank 16 coincides with the central axis of the elongated tip 18 where the shank and the elongated tip are connected. This rotatable attachment may be possible by structures such as one or more bushings, bearings, flanges, washers, magnets, collars, gaskets, or rotatable connectors that connect the elongated tip to the shank while helping actuate or facilitate rotation. Here, the side of the elongated tip may be rolled against a restorative material 42 on a tooth surface 40, in order to evenly distribute the material while avoiding the incorporation of air bubbles. In this embodiment, the elongated tip 18 may furthermore be coated with a non-stick material. In a further embodiment, the elongated tip may be rotatably attached so that its rotation in one direction may decrease the interior volume of the socket 24. In some cases, the interior volume of the socket 24 may be decreased to the point of pushing the ball 20 out. This may be done with an end of the shank 16 having a screw or a rod that slides into the socket 24, and may be used as a way of exchanging the ball or separating the ball and socket for cleaning. In this embodiment, a perimeter of the socket may be coated with an elastomeric material so that the ball 20 does not fall out without a force being applied from within the socket 24 to push the ball outwards.

In one embodiment, the elongated tip 18 is removably attached to the curved and/or angled shank 16. For instance, the elongated tip may be attached to the shank by a screw thread. In other embodiments, the attachment may be an unthreaded fitting secured by a magnet, a clip, a lever, a washer, a spring-loaded latch, and/or an O-ring. The connection may involve a ball-lock coupling, a roller-lock coupling, a pin-lock coupling, a flat-face coupling, a bayonet coupling, a ring-lock coupling, a cam-lock coupling, or some other structure. Preferably the fitting allows a user to separate and connect the elongated tip and the shank without the use of a tool. In an alternative embodiment, the shank may be removably attached to the handle by any of the fittings discussed above.

In some embodiments, where the elongated tip 18 is removably attached to the curved and/or angled shank 16, differently shaped elongated tips may be attached to the shank during the restoration of the tooth, as necessary, to ensure complete and even coverage to an uneven surface. In some embodiments, elongated tips may be color-coded, for example, based on size, ball diameter, surface type, being able to rotate, or other physical features.

In one embodiment, an end of the elongated tip connected to the curved and/or angled shank has a beveled edge 22. FIGS. 3A and 3B show this beveled edge 22. The edge may form a flat surface having an angle of 100°-160°, preferably 120°-150° with the side of the elongated tip 18. In some embodiments, the beveled edge 22 may be connected by a smooth curve as in FIGS. 3A and 3B, rather than by a sharp angle. The longitudinal length of the beveled portion may make up 5-25% preferably 10-20%, more preferably 12-18% of the total longitudinal length of the elongated tip.

In one embodiment, a central axis of the elongated tip 18 forms an angle of 50°-75°, preferably 550-70°, more preferably 60°-66° with a central axis of the handle 12, however, in some embodiments, the angle may be less than 50° or greater than 75°. FIG. 1 shows an embodiment of a dental instrument 10 forming an angle of 60°-66° between the central axis of the elongated tip 18 and the central axis of the handle 12. In an alternative embodiment, the shank 16 may be attached to the handle or the elongated tip by a movable joint, or the length of the shank may comprise one or more movable joints. In this alternative embodiment, the elongated tip 18 may be adjusted to different angles in relation to the central axis of the handle 12.

In one embodiment the handle 12, the curved and/or angled shank 16, the elongated tip 18, and/or the ball 20 is made of, contains, comprises, or is coated with a biocompatible metal or a non-metal. Examples of biocompatible metals include, but are not limited to stainless steel, aluminum, cobalt, zirconium, and titanium. Examples of biocompatible non-metals include but are not limited to polylactic acid (PLA), poly(lactic-co-glycolic acid) (PLGA), polyvinylchloride (PVC), polyethylene terephthalate (PET), acrylonitrile butadiene styrene (ABS), polypropylene (PP), polystyrene (PS), polytetrafluoroethylene (PTFE), polyetheretherketone (PEEK), polyetherketoneketone (PEKK), polycarbonate (PC), silicone, polyurethane, glass, carbon fiber, and/or ceramic. In one embodiment, the non-metal may be a thermoplastic elastomer (TPE) such as a styrenic block copolymer (TPE-s), a thermoplastic olefin (TPE-o), an elastomeric alloy (TPE-v or TPV), a thermoplastic polyurethane (TPU), a thermoplastic copolyester (TPE-E), or a thermoplastic polyamide. Alternatively, the handle 12, the curved and/or angled shank 16, the elongated tip 18, and/or the ball 20 comprises a non-biocompatible metal or non-metal, but the exterior surface of either may be coated with a biocompatible metal or non-metal.

In one embodiment, the handle 12, the curved and/or angled shank 16, the elongated tip 18, and/or the ball 20 comprises a plastic which contains metal, glass, ceramic, carbon, or polymer fibers. The plastic may be any of those previously described, or may be some other plastic. In this embodiment, the plastic may contain 0.001-0.01 wt %, 0.01-0.1 wt %, 0.1-1 wt %, 1-3 wt %, 3-5 wt %, or 5-10 wt % metal fibers, glass fibers, ceramic fibers, carbon fibers, and/or polymer fibers relative to a total weight of the plastic and total fiber content. In some embodiments, the plastic may contain greater than 10 wt % metal, glass, ceramic, carbon, or polymer fibers relative to a total weight of the plastic and fibers. Ideally, this incorporation of fibers into the plastic is to improve durability of the dental instrument or improve an aspect of its manufacturing.

In one embodiment, the handle 12, the curved and/or angled shank 16, the elongated tip 18, and/or the ball 20 is made of, contains, or is coated with a non-stick material. A "non-stick" material, coating, or film is one to which dental materials, such as restorative materials, do not substantially adhere. In one embodiment, this non-stick material may be polytetrafluoroethylene (PTFE), which is commonly known as TEFLON, or may be fluorinated ethylene propylene, perfluoroalkoxy copolymers, carbon fibers, anodized aluminum, ceramic, silicone, an ultrahydrophobic material, or a self-cleaning material. In another embodiment, a non-stick material may be formed by a textured solid surface having an adsorbed impregnating liquid, such as LIQUIGLIDE. In some embodiments, silicone rubber may be considered to be a non-stick material. In a related embodiment, the handle 12, the curved and/or angled shank 16, the elongated tip 18, and/or the ball 20 may be coated with a non-stick lubricant such as a petroleum distillate.

In one embodiment, the handle 12, the curved and/or angled shank 16, the elongated tip 18, and/or the ball 20 is made of, contains, or is coated with at least one material having a Shore A hardness (ASTM D2240 00) ranging from 20-80, preferably 25-75, more preferably 30-70. In other embodiments, the handle 12, the curved and/or angled shank 16, the elongated tip 18, and/or the ball 20 is made of, contains, or is coated with at least one material having a Shore A hardness of less than 20 or greater than 80.

Figure 5:
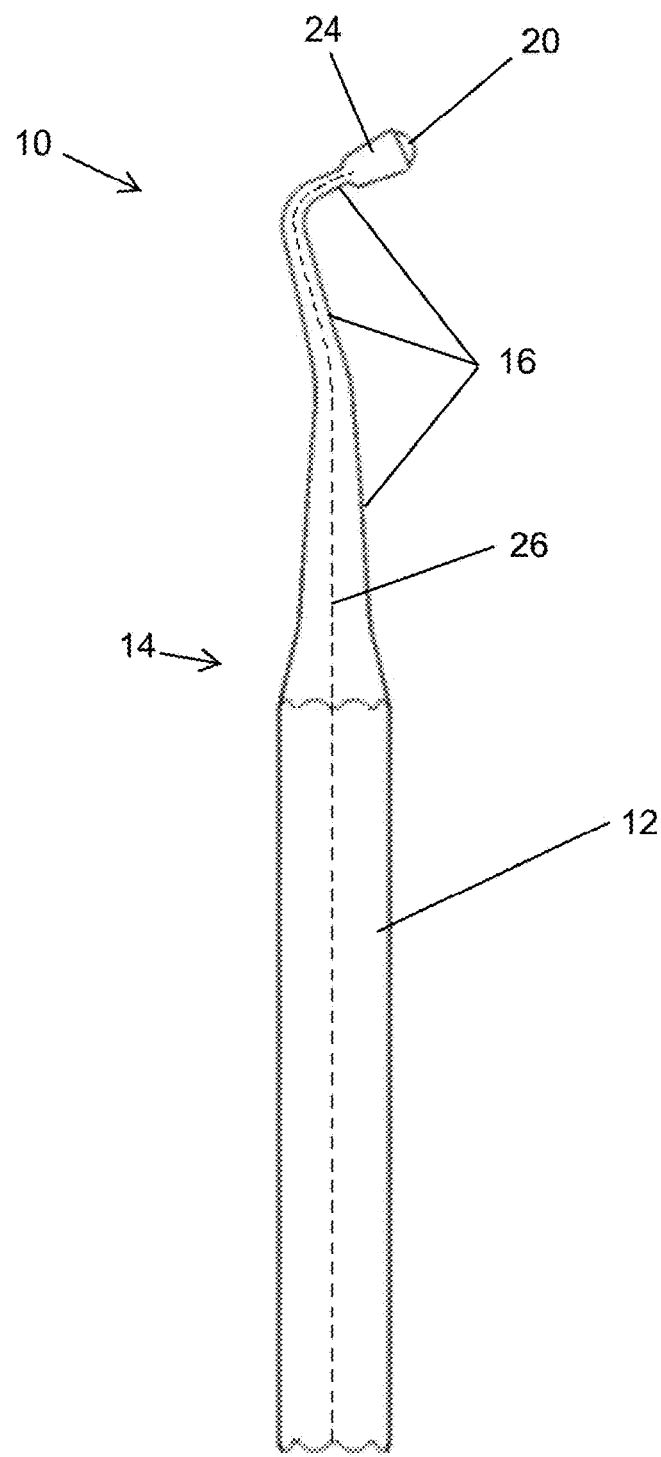
FIG. 5 is a dental instrument with a fluid line traversing from the handle to the socket.

In one embodiment, the dental instrument 10 also has a fluid line 26 traversing from the socket 24 to the handle 12, as shown in FIG. 5. Preferably the fluid line 26 also traverses the shank 16 between the socket 24 and the handle 12, so that the fluid line 26 is completely inside the dental instrument 10. This fluid line 26 may simply be a hole traversing through the dental instrument 10, or the fluid line may be a hole traversing through the dental instrument but lined with a material different than the bulk of the handle, which material may be any of those discussed previously. In an alternative embodiment, the handle 12 and/or shank 16 is hollow, with the fluid line 26 comprising tubing that is threaded through the hollow space. The fluid line may transport a fluid used in dental hygiene and dental surgery procedures, including, but not limited to, air, nitrous oxide, water, saline solution, antiseptic solution, anesthetic solution, fluoride solution, sodium hypochlorite solution, EDTA solution, chlorhexidine solution, hydrogen peroxide solution, citric acid solution, detergent solution, lactated Ringer's solution, povidone-iodine solution, mouthwash, or any combination thereof. In one embodiment, a fluid may be used to set or harden a composite. As used herein, the term "fluid" is defined as a gas, a liquid, a substance which flows, or a substance which differs from a solid in that it can offer no permanent resistance to change of shape. This definition also includes mixtures of gases, mixtures of liquids, and mixtures of gases and liquids. However, in an alternative embodiment, the instrument may deliver a mixture of powder and fluid, for example, glycine or sodium bicarbonate powder and air. In another embodiment, the fluid line may also transport an aspirate taken from the mouth of a patient during a dental procedure. This action may occur by the fluid line containing a negative pressure, or a pressure less than the ambient or atmospheric pressure. The fluid line may have an inner diameter of 0.2 mm-10 mm, preferably 0.5 mm-5 mm, more preferably 0.8 mm-3 mm. The fluid line may accommodate flow rates of up to 20 mL/min, preferably up to 30 mL/min, more preferably up to 40 mL/min, and pressures up to 50 kPa, preferably up to 70 kPa, more preferably up to 90 kPa. In one embodiment, the fluid line may aspirate or deliver a fluid for the purpose of rinsing composite or other materials from the socket, and this rinsing may be done outside and away from a patient. In one embodiment, this rinsing may involve alternating cycles of aspiration and fluid delivery in order to dislodge particles from the socket.

However, in another embodiment, the socket 24 has no more than one opening, which is the opening at the end of the elongated tip where the ball is exposed. This embodiment is shown in FIG. 3B. Here, there is no other opening or a fluid line 26 to the socket 24. Alternatively, in one embodiment, a fluid line 26 may open from a side of the elongated tip 18 rather than connect with the socket 24.

In one embodiment, the dental instrument 10 also has a second curved and/or angled shank 28 extending from an end 36 of the handle distal to the working end 14, having a second elongated tip 32 with a second socket and a second ball 34 rotatably housed within the second socket, having a second exposed surface. In this embodiment, the ball 20 and the second ball 34 have unequal diameters. For instance, the second ball 34 may have a diameter that is 5-50%, preferably 10-40%, more preferably 15-25% larger than the diameter of the ball 20, or the ball 20 may be larger than the second ball 34 by similar percentages. In this embodiment, the dimensions, shapes, compositions, and structures of the second curved and/or angled shank 28, the second socket, and the second ball 34 may be of those previously described, or they may be larger, smaller, or shaped differently. In one embodiment, both ends of the handle may have similar structures and sizes.

In one embodiment, the ball 20 and the second ball 24 may have the same diameter or substantially the same diameter. In a further embodiment, the dental instrument may have an elongated tip 18 and a second elongated tip 32, with both tips being the same shape so that the dental instrument 10 has reflectional symmetry and/or rotational symmetry.

Figure 4A:
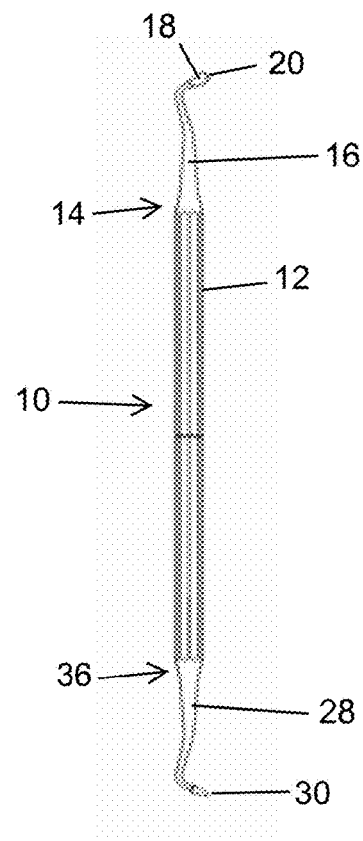
FIG. 4A is a dental instrument having a second tip which is not a second elongated tip and ball.
Figure 4B:
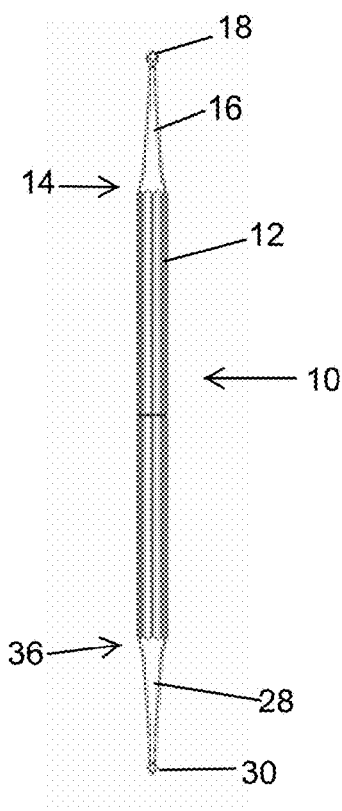
FIG. 4B is a side view of the dental instrument in FIG. 4A.

In related embodiment, the dental instrument 10 has a second curved and/or angled shank 28 extending from an end of the handle distal to the working end 14, having a different instrument tip 30, such as that in the form of a blade, a spike, a spatula, a hook, a fork, a bead, or any combination thereof. In this embodiment, this end of the dental instrument may be used as a plugger, a burnisher, a dental packer, a sinus lift, a curette, a retractor, an elevator, a dental probe, a dental scaler, a dental explorer, a dental chisel, a periotome, a retractor, a sinus lift, a carver, a dental chisel, a dental file, a dental hoe scaler, a dental spreader, a root canal file, a dental packer, an osteotome, a periotome, a root tip pick, a scalpel, drill, a dental mirror, a hemostat, a needle holder, a polisher, a crown remover, a clamp, a camera, a band pusher, a debrider, a ring, a ligature director, or a condenser in a different form or shape than the present invention. FIGS. 4A and 4B show views of a dental instrument 10 having a second working end 36 with a second shank 28 and an instrument tip 30 in the form of a cone or spike.

Figure 7:
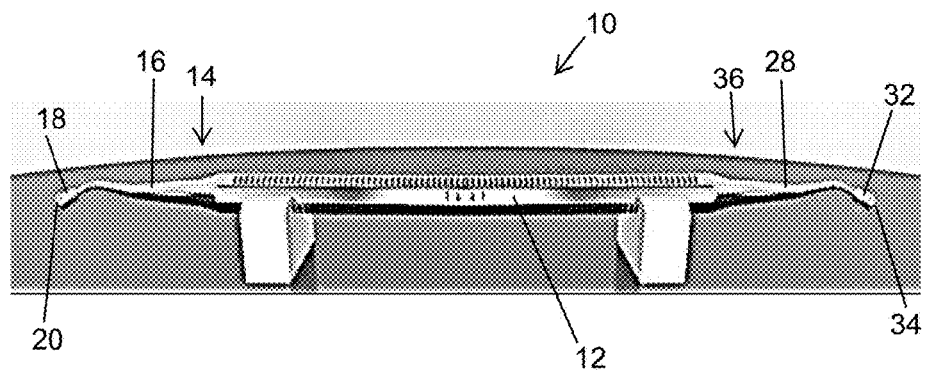
FIG. 7 is a dental instrument having a second working end with a second elongated tip and a second ball.

In one embodiment, the central axis of the elongated tip 18 and/or the central axis of the second elongated tip 32 may independently form an angle of 00-90°, preferably 200-85°, more preferably 400-800 with a central axis of the handle 12. In a further embodiment, the central axis of the elongated tip 18 and/or the central axis of the second elongated tip 32 may independently form an angle of 500-75°, preferably 550-70°, more preferably 60°-67°. These embodiments are shown in FIGS. 1, 5, and 7.

In one embodiment, the central axis of the elongated tip, the central axis of the second elongated tip, and the central axis of the handle lie in the same geometric plane. In a further embodiment of this, the elongated tip 18 and the second elongated tip 32 lie on the same side of the handle, as shown in FIG. 7. In other words, the elongated tip 18 and the second elongated tip 32 are angled in the same general direction. Alternatively, the central axis of the elongated tip, the central axis of the second elongated tip, and the central axis of the handle lie in the same geometric plane, but the elongated tip 18 and the second elongated tip 32 lie on opposite sides of the handle 12. In other words, the elongated tip 18 and shank 16, and the second elongated tip 32 and second shank 28, extend from the handle 12 in generally opposite directions.

Figure 8:
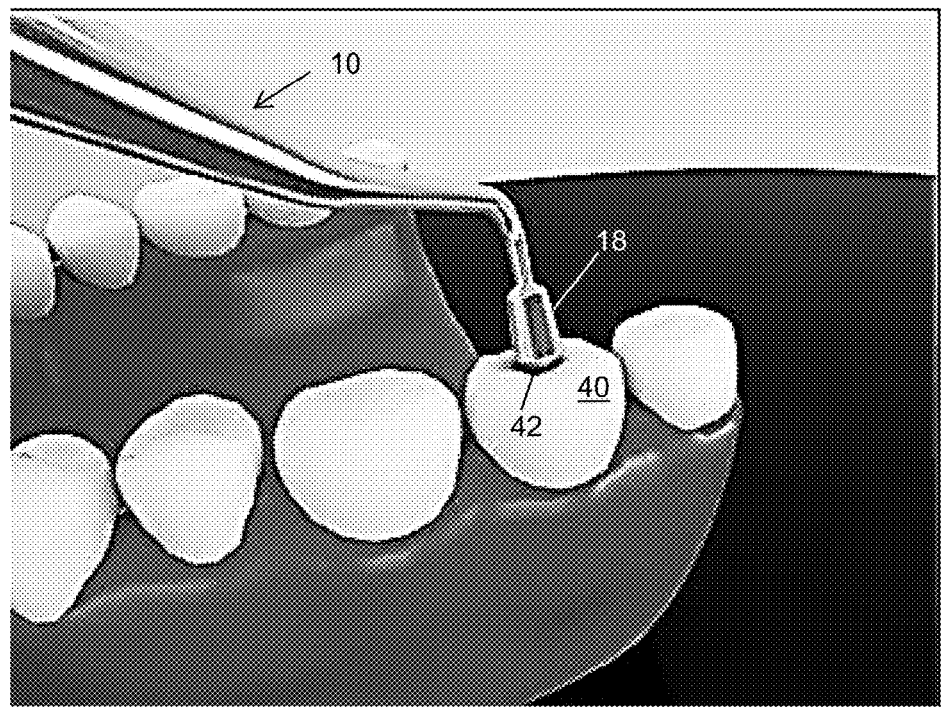
FIG. 8 shows a dental instrument being used to distribute a restorative material on a tooth surface.

According to a second aspect, the present disclosure relates to a method for distributing a restorative material 42 on a surface of a tooth 40. This method involves the steps of applying the restorative material to the surface of the tooth to produce an applied restorative material and distributing the applied restorative material with the dental instrument 10 of the first aspect. Preferably this distributing is done by contacting the applied restorative material with the ball 20 and rolling the ball on the surface of the applied restorative material, as shown in FIG. 8. In the embodiment where the elongated tip 18 is rotatably attached, a side of the elongated tip may be contacted against the applied restorative material and rolled against the applied restorative material. The dental instrument 10, in this use or in other uses, may be considered as a condenser, a plugger, a burnisher, a spreader, a roller, a placement tip, a composite instrument, or as some other instrument or tool.

A "restorative material" in the dental arts may also refer to dental composite resins, synthetic resins, light-curable resins, bone grafts, bioactive glass, adhesives, and cements. Synthetic resins evolved as restorative materials since they are insoluble, aesthetic, insensitive to dehydration, easy to manipulate, and reasonably inexpensive. Composite resins most commonly comprise Bis-GMA and other dimethacrylate monomers (TEGMA, UDMA, HDDMA), a filler material such as silica, and in most current applications, a photoinitiator. Dimethylglyoxime is also commonly added to achieve certain physical properties such as flow ability. Glass ionomer cements may also be used. Further tailoring of physical properties of these materials may be achieved by formulating unique concentrations of each constituent. A restorative material 42 may be applied to a tooth on its own, or may secure an implant to a tooth.

As shown in FIG. 8, the dental instrument 10 is advantageously designed to aesthetically distribute restorative material 42 on a tooth surface 40 while avoiding problems associated with adherence of restorative materials to prior art instruments, such as inhomogeneous distribution and bubble formation. The dental instrument 10 of the invention may be used to distribute restorative materials on a natural tooth surface or on an artificial tooth (implant) surface.

In one embodiment, the size of the dental instrument 10, including the size of the elongated tip 18 and ball 20, may be selected so that it can distribute the restorative material 42 on a tooth surface 40, including into or onto a cavity surface. Most embodiments of the dental instrument 10 of the invention are sized proportionately to human teeth. However, the size of an instrument and its elongated tip 18 and ball 20 may vary depending on the dimensions of the tooth surface or teeth being restored. For example, the dental instrument may be configured to conform to different arch forms of teeth, such as sized to conveniently treat teeth in a squared, tapered or ovoid arc, sized based on the age of the patient, or sized proportionately to any non-human teeth or dental surfaces being treated. A skilled practitioner will be able to size the dental instrument appropriately for use. FIG. 8 provides an example of a dental instrument 10 being used. Generally, the dental instrument 10 will be about the same size as that shown in FIG. 8 relative to the tooth or within a size range of 0.5 to 1.5-times the size depicted in FIG. 8.

This range includes all subranges and intermediate values such as 0.5, 0.6, 0.7, 0.8, 0.9, <1.0, 1.0, >1.0, 1.1, 1.2, 1.3, 1.4, <1.5 and 1.5.

Preferably, the design of the dental instrument 10 of the invention may allow it to conform to safe dental practices. The dental instrument may be made of materials recognized as safe for dental instruments and can be sterilized to avoid introduction of contaminants or cross-contaminants into the mouth of a patient. In some embodiments the instrument is reusable and will be made of materials that can be autoclaved, irradiated, or chemically sterilized between uses. In other embodiments, the dental instrument may be formed as a sterile and disposable product so as to avoid the risk of cross-contamination between patients entirely.

Embodiments of the dental instrument 10 include handheld instruments as well as instruments that may be attached or manipulated by machines, dental equipment, waldos or other devices.

In alternative embodiments, the dental instrument 10 may be used in fields outside dental arts, such as a bone graft applicator in surgery, a cell or gel spreader in biological sciences, or a material spreader in visual or culinary arts.

The invention claimed is:

1. A dental instrument, comprising:
   a handle with a working end;
   a curved and/or angled shank extending from the working end;
   an elongated tip with a socket, wherein the elongated tip is mounted on the curved and/or angled shank, and the elongated tip is frustoconical with a frustoconical surface having a larger diameter oriented towards the ball;
   a ball rotatably housed within the socket, the ball having an exposed spherical surface configured to contact a dental composite;
   a second curved and/or angled shank extending from an end of the handle distal to the working end, having a second elongated tip with a second socket; and
   a second ball rotatably housed within the second socket, having a second exposed spherical surface,
   wherein the ball and the second ball have unequal diameters, and
   wherein an end of the elongated tip connected to the curved and/or angled shank has a beveled edge expanding in a direction towards the ball.

2. The dental instrument of claim 1, wherein the ball has an exposed surface area fraction of 0.25 to 0.42 relative to a total surface area of the ball.

3. The dental instrument of claim 1, wherein a ratio of a diameter of the ball to a largest outer diameter of the elongated tip is 7:10-19:20.

4. The dental instrument of claim 1, wherein a ratio of the smallest diameter of the curved and/or angled shank to the largest outer diameter of the elongated tip is 3:10-4:10.

5. The dental instrument of claim 1, wherein the elongated tip is rotatably attached to the curved and/or angled shank.

6. The dental instrument of claim 1, wherein the elongated tip is removably attached to the curved and/or angled shank.

7. The dental instrument of claim 1, wherein a central axis of the elongated tip forms an angle of 0°-90° with a central axis of the handle.

8. The dental instrument of claim 7, wherein a central axis of the elongated tip forms an angle of 50°-75° with a central axis of the handle.

9. The dental instrument of claim 1, further comprising a fluid line traversing from the socket to the handle.

10. The dental instrument of claim 1, wherein the socket has no more than one opening.

11. The dental instrument of claim 1, wherein the handle, the curved and/or angled shank, the elongated tip, and/or the ball comprises metal.

12. The dental instrument of claim 1, wherein the handle, the curved and/or angled shank, the elongated tip, and/or the ball comprises a plastic which contains metal, glass, ceramic, carbon, or polymer fibers.

13. The dental instrument of claim 1, wherein the handle, the curved and/or angled shank, the elongated tip, and/or the ball is made of, contains, or is coated with a non-stick material.

14. The dental instrument of claim 1, wherein the handle, the curved and/or angled shank, the elongated tip, and/or the ball is made of, contains, or is coated with at least one of a silicone, a thermoplastic elastomer, or a polyurethane.

15. The dental instrument of claim 1 wherein the handle, the curved and/or angled shank, the elongated tip, and/or the ball is made of, contains, or is coated with at least one material having a Shore A hardness of 20-80, as determined by ASTM D2240 00.

16. A method for distributing a restorative material on a surface of a tooth, comprising:
   applying the restorative material to the surface of the tooth to produce an applied restorative material and
   distributing the applied restorative material with the dental instrument of claim 1 by rolling the ball on the applied restorative material.

* * * * *